(12) United States Patent
Tan et al.

(10) Patent No.: US 10,603,073 B2
(45) Date of Patent: Mar. 31, 2020

(54) TROCAR SLEEVE

(75) Inventors: Hock Lim Tan, Kuala Lumpur (MY);
Martin Oberlaender, Engen (DE);
Alexander Fuchs, Steisslingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 879 days.

(21) Appl. No.: 13/485,555

(22) Filed: May 31, 2012

(65) Prior Publication Data
US 2013/0030457 A1  Jan. 31, 2013

Related U.S. Application Data

(63) Continuation-in-part of application No. 13/485,247, filed on May 31, 2012, now abandoned.

(30) Foreign Application Priority Data

May 31, 2011 (EP) .................................... 11168177

(51) Int. Cl.
*A61B 17/34* (2006.01)
*A61B 90/00* (2016.01)

(52) U.S. Cl.
CPC .... *A61B 17/3421* (2013.01); *A61B 2017/346* (2013.01); *A61B 2017/3482* (2013.01);
(Continued)

(58) Field of Classification Search
CPC .............. A61B 17/32053; A61B 17/11; A61B 2017/1107; A61B 17/3496; A61B 17/3421; A61B 17/34; A61B 17/326; A61B 17/3417; A61B 17/3431; A61B 2017/3405; A61B 2017/3407; A61B 2017/3419; A61B 2017/3425; A61B 2017/3427;
(Continued)

(56) References Cited

U.S. PATENT DOCUMENTS

| | | | | |
|---|---|---|---|---|
| 1,798,124 A | * | 3/1931 | Hunn | ............................ 600/226 |
| 5,261,888 A | * | 11/1993 | Semm | ................ A61B 17/3421 |
| | | | | 604/158 |
| 5,312,401 A | * | 5/1994 | Newton | ............. A61B 18/1233 |
| | | | | 606/35 |
| 5,505,689 A | * | 4/1996 | Kramer et al. | ................ 600/204 |
| 5,514,075 A | * | 5/1996 | Moll | .................. A61B 17/0218 |
| | | | | 600/202 |

(Continued)

FOREIGN PATENT DOCUMENTS

| DE | 102009014525 A1 | 9/2010 |
|---|---|---|
| WO | 2010136805 A1 | 12/2010 |

OTHER PUBLICATIONS

European Search Report; Application No. EP 11 16 8177; dated Nov. 9, 2011; dated Nov. 18, 2011; 4 pages.

*Primary Examiner* — Tan-Uyen T Ho
*Assistant Examiner* — Chima U Igboko
(74) *Attorney, Agent, or Firm* — Whitmyer IP Group LLC (57) ABSTRACT

A trocar sleeve for minimally invasive surgery, having a first sleeve part, which has essentially the shape of a straight tubular piece with a longitudinal axis, and having a second sleeve part, which at least partly surrounds the first sleeve part in close contiguity and is movable during use with respect to the first sleeve part. The mobility of the second sleeve part in relation to the first sleeve part consists essentially only in rotatability of the second sleeve part around the first sleeve part, and in addition the first sleeve part and the second sleeve part each comprise on their distal axial ends a flange part that extends radially outward at an angle of less than 180 degrees from the respective sleeve part.

21 Claims, 11 Drawing Sheets

(52) U.S. Cl.
CPC ............... *A61B 2017/3484* (2013.01); *A61B 2017/3492* (2013.01); *A61B 2090/0817* (2016.02)

(58) Field of Classification Search
CPC .... A61B 2017/3429; A61B 2017/3433; A61B 2017/3435; A61B 2017/3441; A61B 2017/3443; A61B 2017/3447; A61B 2017/345; A61B 2017/3452; A61B 2017/3492; A61B 2017/3482; A61B 2017/3484; A61B 2017/3488; A61B 2017/349; A61B 2017/3486; A61B 17/3201; A61B 17/2816; A61B 17/2812; A61B 17/2808; A61B 2017/346; A61B 2090/0817
USPC ........ 600/204, 184, 188, 193, 196; 606/108, 606/191, 198
See application file for complete search history.

(56) References Cited

U.S. PATENT DOCUMENTS

| | | | |
|---|---|---|---|
| 5,716,326 A * | 2/1998 | Dannan ............... | A61B 17/0281 600/204 |
| 5,941,819 A * | 8/1999 | Chin ............................ | 600/204 |
| 6,228,063 B1 * | 5/2001 | Aboul-Hosn ...... | A61B 17/3423 604/174 |
| 2002/0042606 A1 | 4/2002 | Castaneda et al. | |
| 2004/0042606 A1 | 3/2004 | Zino et al. | |
| 2005/0273132 A1 * | 12/2005 | Shluzas et al. ................ | 606/198 |
| 2006/0276818 A1 * | 12/2006 | Buser .................. | A61B 17/3417 606/185 |
| 2007/0162066 A1 | 7/2007 | Lyon | |
| 2008/0058730 A1 * | 3/2008 | Melsheimer ........ | A61B 17/3417 604/177 |
| 2008/0234550 A1 * | 9/2008 | Hawkes et al. ................ | 600/204 |
| 2008/0242930 A1 * | 10/2008 | Hanypsiak .......... | A61B 17/3421 600/114 |
| 2012/0010471 A1 * | 1/2012 | Mire et al. .................... | 600/210 |

* cited by examiner

TROCAR SLEEVE

CROSS-REFERENCE TO RELATED APPLICATIONS

The present application is a continuation-in-part of the pending U.S. patent application Ser. No. 13/485,247, filed May 31, 2012 now abandoned, which application claims priority from German patent application No. 11 168 177.1 filed on May 31, 2011. The content of all prior applications is incorporated herein by reference.

FIELD OF THE INVENTION

The invention relates to a trocar sleeve for minimally invasive surgery, having a first sleeve part that essentially has the form of a straight tubular piece with a longitudinal axis, and having a second sleeve part that at least partly surrounds the first sleeve part in close contiguity with it and is movable during use in relation to the first sleeve part.

BACKGROUND OF THE INVENTION

A trocar sleeve of this type is known from patent WO 2010/136805 A1, although the two sleeve parts are two telescope-type straight tubular pieces that can slide into and out of one another and whose relative sliding either follows a straight line or moves along a helical spiral. The radial outer sleeve part is connected on its proximal end with a head piece that comprises an insulation for gas-tight insertion of an instrument into the trocar sleeve and a fluid connection support, and the radially inner sleeve part has a flexible ring-shaped flange on its distal end.

A trocar sleeve is a medical instrument that is used in minimally invasive surgery for inserting instruments into the human or animal body. In a minimally invasive surgical procedure, a trocar, which consists of a trocar sleeve and a trocar mandrel that is enclosed in the trocar sleeve, is used, first, to provide access to a body cavity. For this purpose the tip of the trocar mandrel is applied on an incision on the skin and is then pushed through the epithelium. Then the trocar mandrel is withdrawn from the trocar sleeve; the trocar sleeve remains inserted in the body. Through the trocar sleeve it is then possible to insert, in alternation, instruments such as endoscopes, forceps, scissors, sewing instruments and the like into the body cavity to perform surgical procedures.

The flexible flange on the distal end of a trocar sleeve unfolds below the perforated epithelium and can then be secured with a corresponding additional flange from outside in order to ensure secure anchoring on the epithelium. To make it possible for the flange to unfold below the epithelium, the trocar sleeve must be slid relatively deeply into the body, and in addition a flexible flange made of rubber or the like must be relatively thick to allow it to be effectively secured from outside, so that the flange, even during an intervention, takes up relatively much space below the epithelium. In addition, most trocar sleeves are designed for a certain minimum thickness of the epithelium. For these reasons the known trocar sleeves are not suited for some operations, for instance operations on small children or on the thyroid.

The documents US 2008/0242930 A1, DE 10 2009 014 525 A1 and US 2002/0042606 A1 each disclose an instrument for providing access for surgical interventions, said access comprising two elements that can pivot around an axis running perpendicular to the instrument longitudinal axis and that can be unfolded below the epithelium to form a type of flange, likewise requiring relatively a great deal of space below the epithelium.

SUMMARY OF THE INVENTION

It is the object of the invention to provide a trocar sleeve that requires a very small insertion depth and no minimum thickness of the epithelium and that is also simple to produce, easy to install and can be cleaned well.

This object is achieved by means of a trocar sleeve with the characteristics of claim 1. Advantageous refinements of the invention are indicated in the dependent claims.

According to the invention, the two sleeve parts each comprise on their distal axial ends a flange part that extends outward at an angle of less than 180 degrees from the respective sleeve part. If the sleeve parts are turned into a relative position in which both flange parts point in the same direction and essentially are situated one above the other congruently, the two flange parts together can be slid through and below the epithelium without needing to be flexible, because the elasticity of the epithelium is sufficient in itself. This is particularly true when the flange parts, as preferred, have approximately U-shaped contours, as seen in a plane perpendicular to the longitudinal axis, such that the distance of the two legs of the U-shape is approximately equal to the diameter of the first or preferably of the second sleeve part.

After insertion, the sleeve parts can easily be turned by hand into a relative position in which the two flange parts point in contrary directions to one another and are situated in a plane perpendicular to the longitudinal axis, so that the trocar sleeve is anchored on the perforated epithelium.

Because the flange parts are not required to be flexible, they can be made of a stable material just like the sleeve parts and thus are preferably of one-piece construction. Flange parts of this type can be substantially thinner than a flexible flange, for example approximately 1 mm thick. In the insertion position in which the two flange parts are situated directly one above the other, their total thickness is then equal to 2 mm, which is still comparatively little, so that the trocar sleeve has a very small insertion depth in a body.

According to the invention, the mobility of the second sleeve part in relation to the first sleeve part consists essentially only in an ability of the second sleeve part to rotate around the first sleeve part. With respect to the foregoing, this should be understood as indicating that it is harmless to have an axial mobility that serves in the course of the rotation to bring only one of the two flange parts, which are situated in insertion position one above the other, into the working position, in precisely the same plane as that of the other flange part, in order to produce a plane anchoring surface below the epithelium. In the cited example of flange parts 1 mm thick, a sliding of this type would be equal to 1 mm. It is likewise harmless when, in the course of a rotation, between the insertion position and the working position, there is a particular installation position in which the second sleeve part can be slid in the axial direction in order to be able to release it easily from the first sleeve part and the head part. It is useful to provide an installation position of this type in order to allow the trocar sleeve to be assembled easily and dismantled again quickly for cleaning.

In theory, each of the two sleeve parts can comprise essentially, that is as one base body, a straight full tube. In this case the first, inner sleeve part must be detachably fastened on the body part, for example by means of cap nuts and positioning pins so that the second sleeve part can be installed and dismantled.

In an alternative embodiment, the portion of the second sleeve part that is contiguous with the first sleeve part is essentially in the form of a half of a lengthwise two-part tube. In this case the second sleeve part can simply be slid axially over the first sleeve part and along the longitudinal axis in the direction toward the head part of the trocar sleeve and then allowed to engage in the guide and locking means configured in the head part.

The cross-section of the second sleeve part perpendicular to the longitudinal axis can be, for example, simply a semicircle.

It is better for the cross-section of the second sleeve part perpendicular to the longitudinal axis to be a circular arc, which comprises a few more degrees than a semicircle. In this case the second sleeve part surrounds the first sleeve part at an angle of something more than 180 degrees and is thereby held firmly in form-locked manner on the first sleeve part along its entire length, also ensuring good cohesion of the two sleeve parts during use. To facilitate the axial sliding of the second sleeve part onto the first sleeve part, the flange part of the first sleeve part can be provided with small indentations at the point where it makes a transition into the first sleeve part.

Optimal gas-proof insulation between the trocar sleeve and the body opening held open by it, can be achieved with an embodiment in which each of the two sleeve parts has essentially the shape of a straight full tube, such that the first, inner sleeve part is detachably fastened on the head part and the second sleeve part can be assembled on and disassembled from the first sleeve part when the first sleeve part is separated from the head part.

In this case the second sleeve part is preferably guided in such a way that it can be rotated between two end positions that are situated about 180 degrees apart with respect to the longitudinal axis, such that the one end position corresponds to an insertion position in which the flange parts of the first and second sleeve parts point in the same direction and are situated precisely in a plane perpendicular to the longitudinal axis, and such that the other end position corresponds to a working position in which the flange parts of the first and second sleeve parts point in approximately opposite directions to one another and likewise are situated in a plane precisely perpendicular to the longitudinal axis. Here the flange parts of the first and second sleeve parts have, preferably together, a U-shaped radial contour as seen in a plane perpendicular to the longitudinal axis.

The detachable fastening of the first sleeve part on the head part can include a screw-in lock or a type of bayonet lock.

A trocar mandrel especially suitable for the invention has a blunt distal end whose contour concludes essentially flush with the contour of the distal end of the trocar sleeve when the trocar mandrel is inserted completely into the trocar sleeve.

To secure the flange parts on the outside of the epithelium, it is possible in principle to use any disc-shaped element, in particular a two-part element, that can be installed around the sleeve parts after assembly of the second sleeve part.

Especially useful for the invention, however, is a securing element in the form of a one-piece, rubber disc, with gap, which can be slid laterally over the sleeve parts of the trocar sleeve with the gap stretched wide and then closes more or less firmly around the sleeve parts because of its own elasticity. After the trocar sleeve has been anchored in the epithelium, the rubber disc is simply slid along the longitudinal axis in the direction toward the epithelium in order to protect the flange part from outside the epithelium. The rubber disc then remains in this position simply by static friction.

Even more useful, because it attaches with particular reliability on the sleeve parts, is a securing element made of a rigid element with a gap that fits with the outer diameter of the outer sleeve part and with an elastic element that can be detached from the rigid element, or alternatively made only of rigid elements, namely a plate with a gap that fits with the outer diameter of the outer sleeve part, a clamping element for the outer sleeve part that can be slid onto the plate, and an actuation element mounted on the plate for the slidable clamping element. Securing elements of this type are also useful for other trocar sleeves and trocars as described herein.

Because it is possible to dismantle the trocar sleeve, and the additional parts that form a trocar, easily and rapidly into their components, said parts are also easy to clean, so that the trocar sleeve or the trocar constructed with it meets stringent hygienic requirements.

BRIEF DESCRIPTION OF THE DRAWINGS

There follows a description of embodiments with reference to the drawings. The drawings are as follows.

DETAILED DESCRIPTION OF THE INVENTION

The trocar sleeve shown in FIGS. 1 through 6 consists of a head part 2, a first, inner sleeve part 4 and a second, outer sleeve part 6.

The head part 2 is an approximately rotation-symmetrical housing that contains an axial clearance hole. Situated in a proximal end of the head part 2, shown in the upper part of FIGS. 3 through 6, is a flexible insulation 8 for gas-tight insertion of an instrument in and through the clearance hole in the head part 2. In addition, the head part 2 has a fluid connection support 10 with a valve 12. Carbon dioxide or flushing liquid, for example, can be supplied by way of the fluid connection support 10.

Attached to the distal end of the head part 2 is a proximal end of the inner sleeve part 4, which consists mainly of a piece of tube that extends in the axial extension of the clearance hole in the head part 2 to a distal end.

All the way at the distal end of the inner sleeve part 4, a first flange part 14 is shaped that has approximately the form of a spatula. In particular, the flange part 14 has a U-shaped contour, as seen in a plane perpendicular to the longitudinal axis of the inner sleeve part 4, such that the distance between the two legs of the U-shape is equal to or somewhat smaller than the diameter of the inner sleeve part 4. In the embodiment the first flange part 14 consists of the same material as the inner sleeve part 4 and is, for example, 1 mm thick.

The outer sleeve part 6 consists mainly of a lengthwise halved piece of tube of about the same length and of the same material as the inner sleeve part 4. The cross-section of the outer sleeve part 6 perpendicular to the longitudinal axis is a circular arc, which is a few degrees greater than a half-circle. The inner diameter of the outer sleeve part 6 is equal to the outer diameter of the inner sleeve part 4.

On the distal end of the outer sleeve part 6, a second flange part 16 is shaped, which has practically the same contour and the same thickness as the first flange part 14 and, in the same manner that the first flange part 14 forms a right-angle deviating continuation of the inner sleeve part 4, it forms a radially outward running and thus right-angle deviating continuation of the outer sleeve part 6.

In the vicinity of the proximal end of the outer sleeve part 6, a gripping member 18 is shaped on it and, similarly as the second flange part 16, forms a radially outward running continuation of the outer sleeve part 6, but is thicker and wider. Somewhat closer to the proximal end of the outer sleeve part 6, a small, round stud 20 is formed on it and extends a few millimeters axially from the outer sleeve part 6.

The head part 2 on its distal end has a ring 22, with gap, that extends radially around the inner sleeve part 4 at a distance that is somewhat greater than the thickness of the outer sleeve part 6. Interacting with the stud 20 on the outer sleeve part 6, the ring 22 with gap forms guide and locking elements for the outer sleeve part 6 in the manner of a bayonet lock, as is described in greater detail below.

Figures 1, 2:
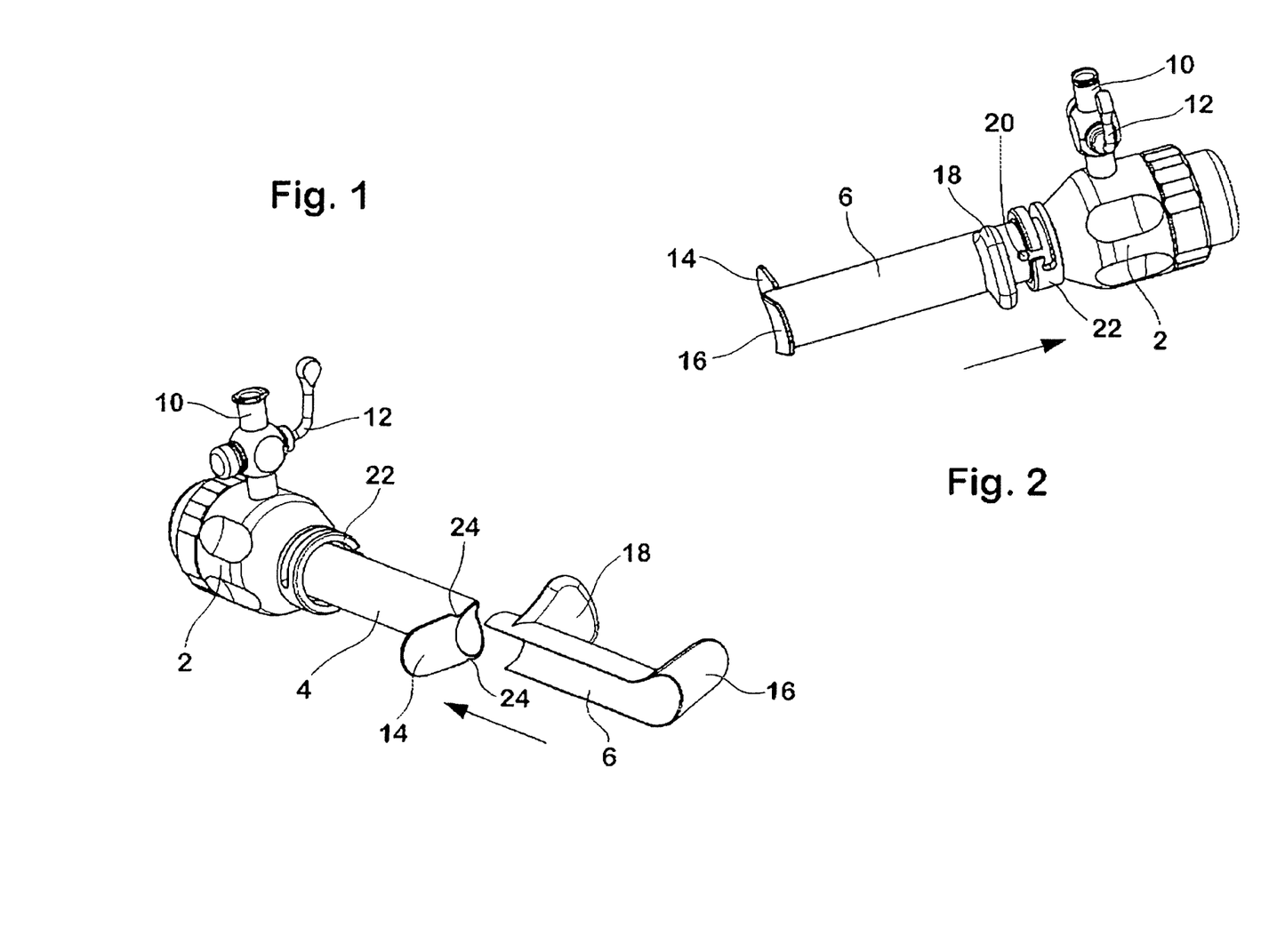
FIG. 1 shows a perspective view of a trocar sleeve whose outer sleeve part is separated from it and is in a position before assembly.
FIG. 2 shows a perspective view of the trocar sleeve of FIG. 1 in an assembly position, that is, in a phase shortly before it is completely assembled.

As shown in FIGS. 1 and 2, the trocar sleeve is installed by sliding the outer sleeve part 6 in the indicated direction of the arrow onto the inner sleeve part 4, so that both flange parts 14, 16 point in directions approximately opposite to one another.

To facilitate this pushing motion, the first flange part 14 has two small indentations 24 in its edges, specifically located where it is connected with the first sleeve part 4. The indentations 24 also allow rotation of the outer sleeve part 6 by a few degrees when it is seated on the inner sleeve part 4. In particular, the outer sleeve part 6 can be rotated into the position shown in FIG. 2, in which both flange parts 14, 16 point in directions about 160 degrees apart, and then the outer sleeve part 6 can be pushed completely onto the inner sleeve part 4.

Figure 3:
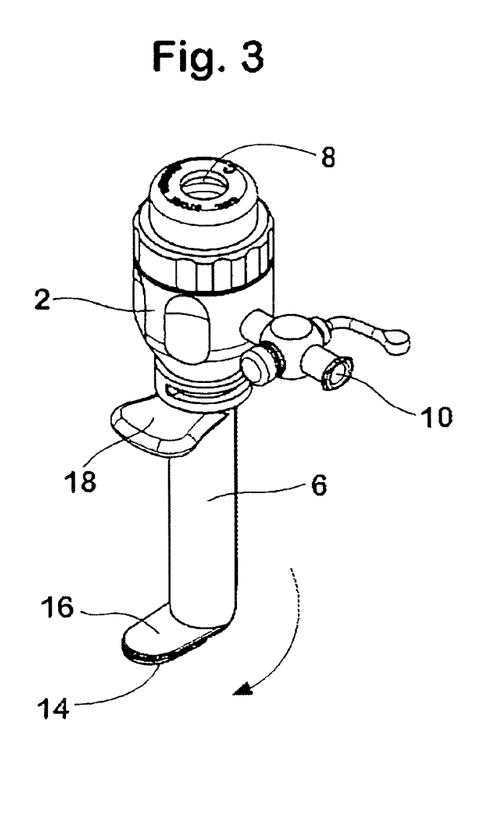
FIG. 3 shows a perspective view of the assembled trocar sleeve with the outer sleeve part in an insertion position in which the trocar sleeve can be inserted into an opening produced in an epithelium.

When the outer sleeve part 6 has been pushed completely onto the inner sleeve part 4, the outer sleeve part 6 is rotated around the inner sleeve part 4 into the position shown in FIG. 3, in which the two flange parts 14 and 16 are situated congruently one over the other. During the rotation, whose rotating direction is indicated in FIG. 3 with an arrow, the stud 20 glides within the ring 22 with gap and is guided thereby.

In the position shown in FIG. 3, the two flange parts 14 and 16 of the trocar sleeve can easily be inserted into an opening produced in an epithelium without penetrating deep therein, while the trocar sleeve is held more or less perpendicular over the epithelium and is moved somewhat downward and to the side so that the two flange parts 14 and 16 together glide below the epithelium.

Figure 4:
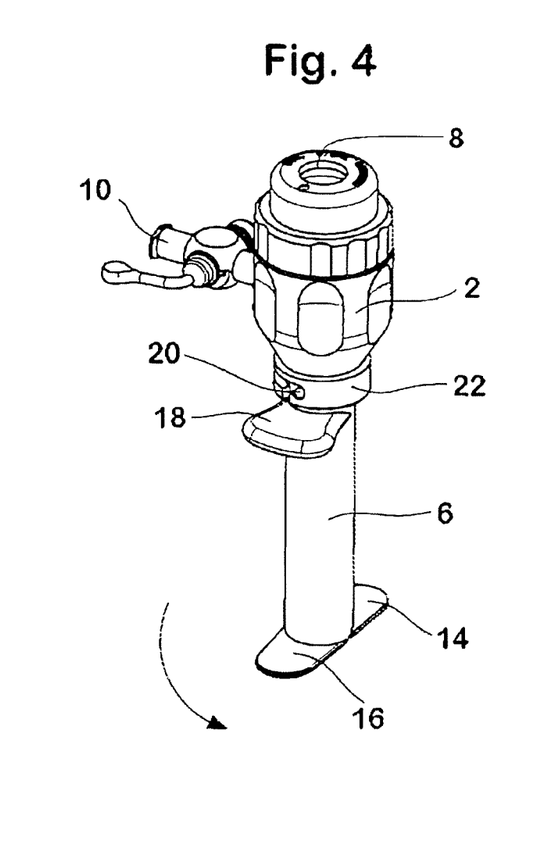
FIG. 4 shows a perspective view of the assembled trocar sleeve with the external sleeve part in a working position, in which the trocar sleeve can be anchored behind an opening produced in an epithelium.

After the trocar sleeve has reached its end position in and above the body opening, the outer sleeve part 6 is rotated back, with the assistance of the gripping member 18, around the inner sleeve part 4, namely into the position shown in FIG. 4 in which the two flange parts 14 and 16 are pointing in directions exactly opposite to one another and are situated precisely in a plane perpendicular to the longitudinal axis of the sleeve parts 4 and 6. The rotation direction is indicated with an arrow in FIG. 4. In this position the stud 20 is held firmly on the first sleeve part 4 by an indentation in the ring 22 with gap, so that the second sleeve part 6 is locked on the trocar sleeve. Within the boundaries dictated by its own elasticity, the second sleeve part 6 is also locked along its length, because the outer sleeve part 6 encloses the inner sleeve part 4 by more than 180 degrees.

The guiding effect of the ring 22 with gap on the head part is either purely rotational or it also causes a slight longitudinal sliding by the thickness of the flange parts 14 and 16, so that the second flange part 16 is automatically moved from the position shown in FIG. 3, in which it is situated congruently over the first flange part 14, into the position shown in FIG. 4, in which it is situated precisely in a plane with the first flange part 14. A displacement of this type can also be achieved by corresponding configuration of the section of the ring 22, with gap, in which the stud 20 is locked by an indentation in the ring 22 with gap.

Figure 5:
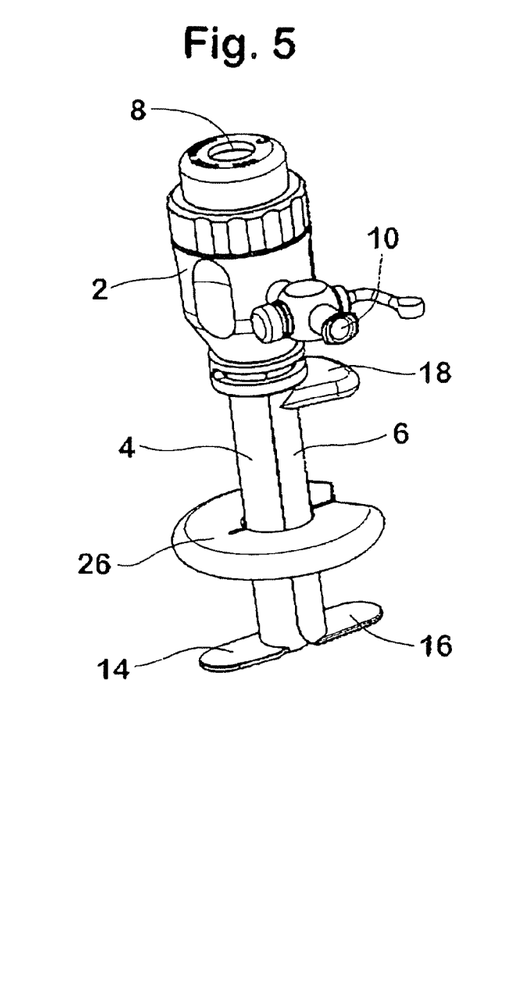
FIG. 5 shows a perspective view of the trocar sleeve from FIG. 4 with a superimposed rubber disc as securing element.
Figure 6:
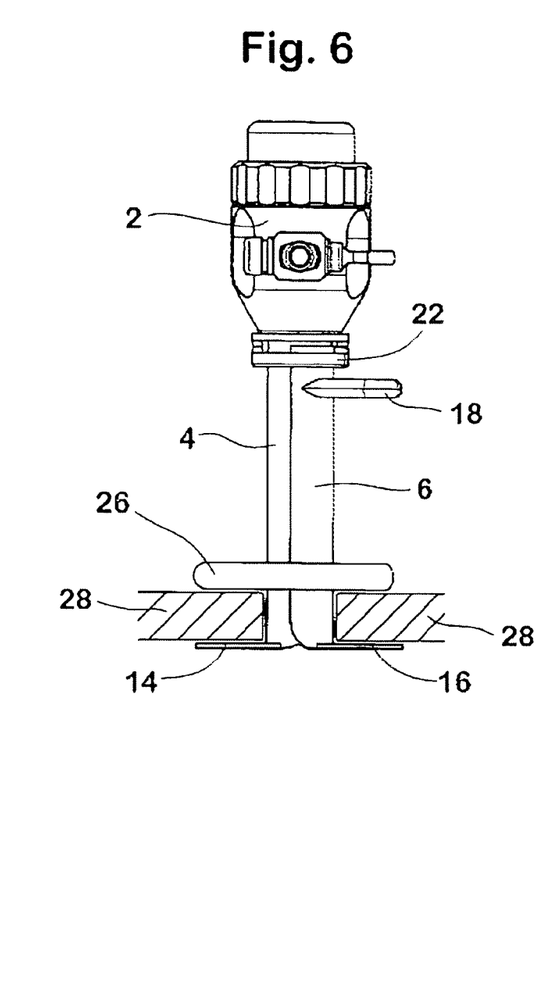
FIG. 6 shows a side view of the trocar sleeve from FIG. 5 as it is anchored and secured in an epithelium.

As shown in FIG. 5, after anchoring the trocar sleeve in a body opening, a with gap, rubber disc 26, in the form of a so-called optic stopper for instance, which can be stretched by hand, is pushed from the side over both sleeve parts 4 and 6 of the trocar sleeve. When the rubber disc 26 contracts again, it surrounds the sleeve parts 4 and 6 with a certain force. The rubber disc 26 can then be pushed by hand in the direction toward the flange parts 14 and 16 until an epithelium 28, indicated schematically in a sectional view in FIG. 6, is contiguous with the flange parts 14, 16 below and with the rubber disc 26 above, so that the trocar sleeve is securely anchored on the epithelium 28.

Instead of the rubber disc 26, any other suitable securing element can be used, for example a two-part securing element, which can be installed around the sleeve parts 4 and 6.

In the illustrated embodiment, the flange parts 14 and 16 are spatula-shaped or U-shaped. Although this special configuration is particularly advantageous in terms of sparing tissue and avoiding great insertion depth in the epithelium, other contour shapes are also possible. For example, the flange parts 14 and 16 can be of any leaf shape, as occurs with plant leaves, but their contours should be rounded. It is essential that each flange part 14, 16 extends radially outward at an angle of less than 180 degrees from the respective sleeve part 4 or 6.

In the illustrated embodiment, the flange parts 14 and 16 are in addition level and situated always parallel to one another. They could also, for example, form conical parts or spherical parts, which could be advantageous for operations on more convex or concave body parts.

An additional embodiment is distinguished from the embodiment in FIGS. 1 through 6 essentially in that the base body of the outer sleeve part does not have a semicircular cross-section, as in the outer sleeve part 6, but instead, as with the inner sleeve part 4, is a full tube. To be able to assemble and dismantle the outer sleeve part in this case, the distal end of the inner sleeve part must be detachably fastened on the head part, for example by means of cap nuts and positioning pins.

This embodiment, which is distinguished in further details from the embodiment in FIGS. 1 through 6, is described in greater detail hereinafter with reference to FIGS. 7 through 26.

Figure 7:
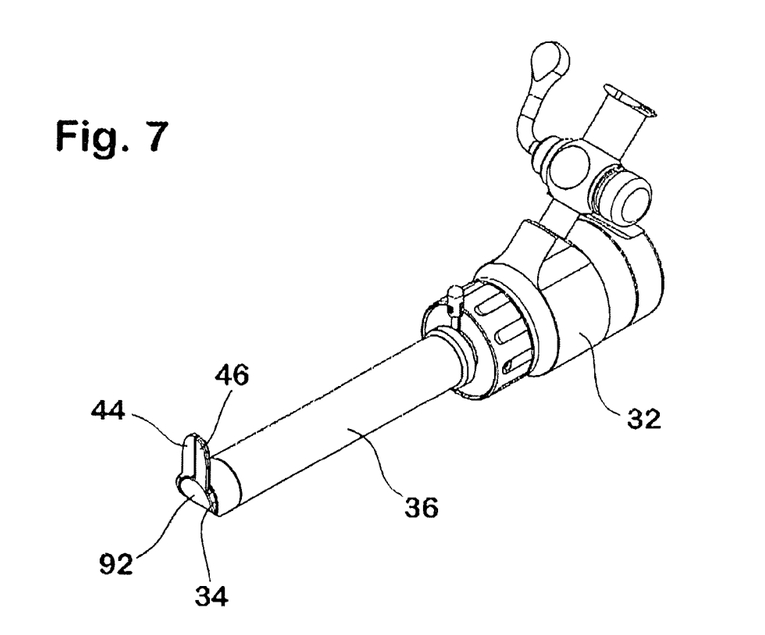
FIG. 7 shows a perspective view of an embodiment for a trocar sleeve in which each of the two sleeve parts has essentially the shape of a straight full tube, in an assembled condition, whereby the outer sleeve part is in an insertion position in which the trocar sleeve can be inserted into an opening produced in an epithelium.

The trocar sleeve with two full tubes as sleeve parts contains a head part 32, a first, inner sleeve part 34 and a second, outer sleeve part 36. The head part 32 is similar to the head part 2 of the foregoing embodiment, except that the inner sleeve part 34, which consists principally of a piece of tube that extends in the axial extension of the clearance hole in the head part 32 all the way to a distal end, is detachably assembled on the distal end of the head part 2. The outer sleeve part 36, like the inner sleeve part 34, has the form of a full tube, and the inner sleeve part 34, beginning with its distal end, can be inserted into the outer sleeve part 36, such that the outer sleeve part 36 encloses the inner sleeve part 34 with little play.

Figures 11, 12:
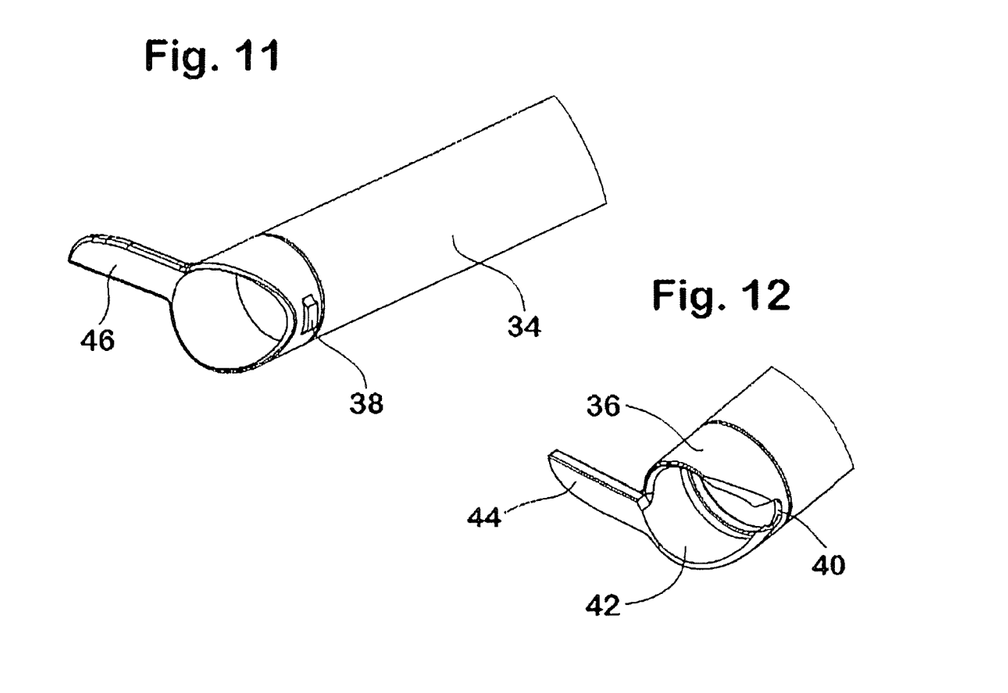
FIG. 11 shows an enlarged perspective view of the distal end of the inner sleeve part of the trocar sleeve from FIG. 7.
FIG. 12 shows an enlarged perspective view of the distal end of the outer sleeve part of the trocar sleeve from FIG. 7.

A first flange part 44 is formed on the distal end of the inner sleeve part 34, said flange part having approximately the shape of a spatula longitudinally cut in half and forming a continuation of the inner sleeve part 34 that runs radially outward and thus protrudes at a right angle. A second flange part 46 is formed on the distal end of the outer sleeve part 36, said flange part having the shape of the other half of the spatula longitudinally cut in half and forming a continuation of the outer sleeve part 36 that runs radially outward and thus protrudes at a right angle.

When the inner sleeve part 34 and the outer sleeve part 36 are completely pushed together lengthwise, as shown in FIGS. 7 through 10, 13 and 14, both flange parts 44 and 46 extend precisely in a plane perpendicular to the longitudinal axis of the sleeve parts 34 and 36.

In the insertion position shown in FIGS. 7, 8, 9 and 14, the two flange parts 44 and 46 supplement one another to form the (halved) spatula, in that they together have a U-shaped contour, as seen in a plane perpendicular to the longitudinal axis of the sleeve parts 34 and 36, such that the distance between the two legs of the U-shape is approximately equal to, or somewhat smaller than, the diameter of the inner sleeve part 34.

The side of the inner sleeve part 34 that is opposite the flange part 44 has a protruding nose 38, which fits into a groove 40 open to the distal end, which is configured in the side of the outer sleeve part 36 opposite the flange part 44. The groove 40 merges into a radially surrounding indentation 42 in the inner circumference of the outer sleeve part 36.

In the relative angular position shown in FIGS. 7 through 10, 13 and 14, the inner sleeve part 34 and the outer sleeve part 36 can be completely pushed together lengthwise, such that the nose 38 slides into the groove 40 and makes contact with its base. At the same time, the plane surface on the flange part 44 of the inner sleeve part 34 that points in the proximal direction makes contact with a distal front end of the outer sleeve part 36. Both flange parts 44 and 46 are then situated in the same plane perpendicular to the longitudinal axis of the sleeve parts 34 and 36.

Figures 9, 10:
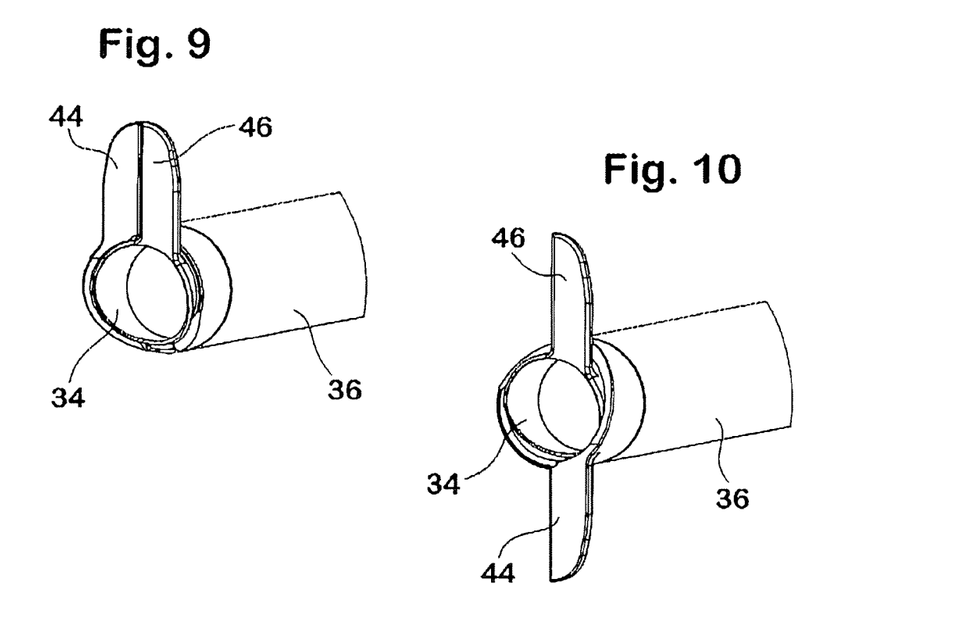
FIG. 9 shows an enlarged perspective view of the distal end of the trocar sleeve from FIG. 7 in the insertion position.
FIG. 10 shows an enlarged perspective view of the distal end of the trocar sleeve from FIG. 7 in a working position in which the trocar sleeve can be anchored behind an opening produced in an epithelium.
Figure 13:
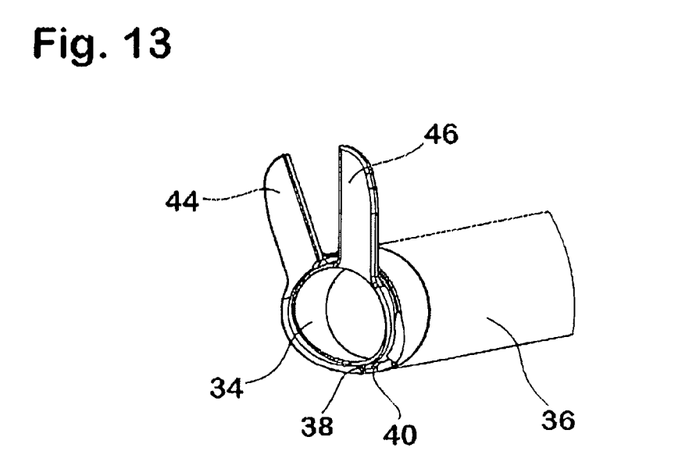
FIG. 13 shows an enlarged perspective view of the distal end of the trocar sleeve from FIG. 7 in the course of a rotation of the outer sleeve part from the insertion position into the working position.

If now the outer sleeve part 36 is rotated somewhat around the inner sleeve part 34 as shown in FIG. 13, the nose 38 on the inner sleeve part 34 enters into the indentation 42 in the outer sleeve part 36, so that the inner sleeve part 34 and the outer sleeve part 36 can no longer be pushed axially toward one another. The outer sleeve part 36 can then be rotated further around the inner sleeve part 34 until the two flange parts 44 and 46 are situated in a working position or operating position, in which they point in directions contrary to one another as shown in FIG. 10, in order to anchor the trocar sleeve below an epithelium. During the entire rotation process, both flange parts 44 and 46 remain in the same plane perpendicular to the sleeve longitudinal axis.

When the inner sleeve part 34 is fastened on the head part 32, then in the insertion position in which the nose 38 does not yet engage in the indentation 42, an axial sliding of the outer sleeve part 36 in the proximal direction is restricted by the head part 32.

Figure 14:
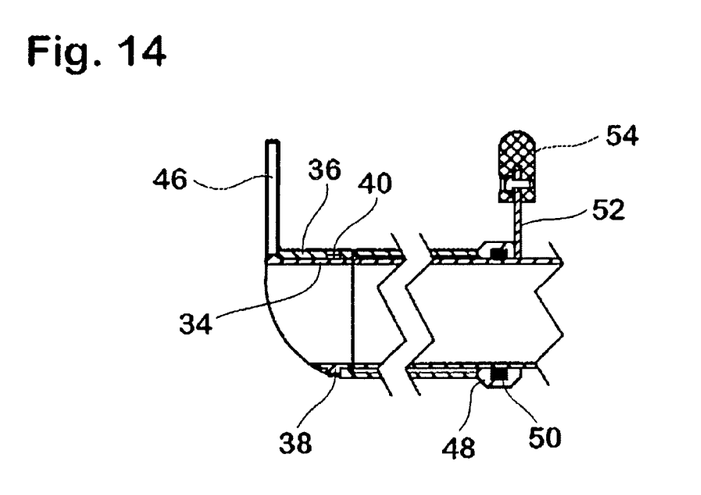
FIG. 14 shows an interrupted longitudinal sectional view of the two sleeve parts of the trocar sleeve in the position from FIGS. 7 and 9.

As shown in FIG. 14, there is, situated on the proximal end of the outer sleeve part 36, a radially surrounding cuff 48 into which an O-ring 50 fits that insulates the outer sleeve part 36 from the longer inner sleeve part 34. Also fastened on the cuff 48 is an actuation lever to turn the external sleeve part 36. Said actuation lever consists of a metallic spring 52 that springs in the sleeve longitudinal direction, with a round plastic cap 54 whose function is explained further below.

There are several possibilities for fastening the inner sleeve part 34, on which the outer sleeve part 36 is mounted, on the head part 32. Described below with reference to FIGS. 15 through 18 is an example for fastening the inner sleeve part 34 on the head part 32 by means of a screw-in lock.

Figure 15:
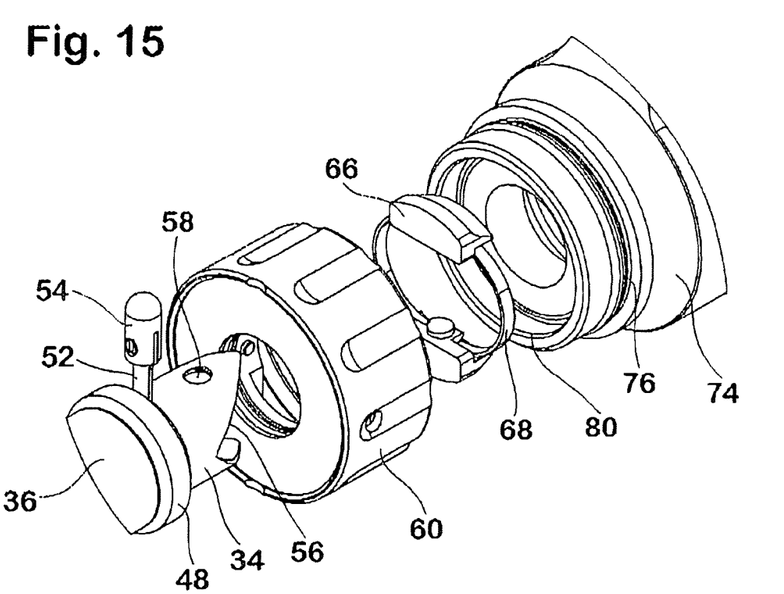
FIG. 15 shows an explosion perspective view of the trocar sleeve from FIG. 7 in the area of the fastening of the inner sleeve part on the head part.

The proximal end of the inner sleeve part 34 with the outer sleeve part 36 assembled on it can be recognized in FIG. 15. The proximal end of the inner sleeve part 34 has a double-V-shaped contour 56 with two locking holes 58 in the peaks of the double-V-shaped contour 56. A cap nut 60, in whose smallest diameter the inner sleeve part 34 fits precisely, has on its inside two pins 62 (FIG. 16) that protrude radially inward beyond the smallest diameter. The indents in the double-V-shaped contour 56 are rounded with the same radius as the pins 62.

Figure 16:
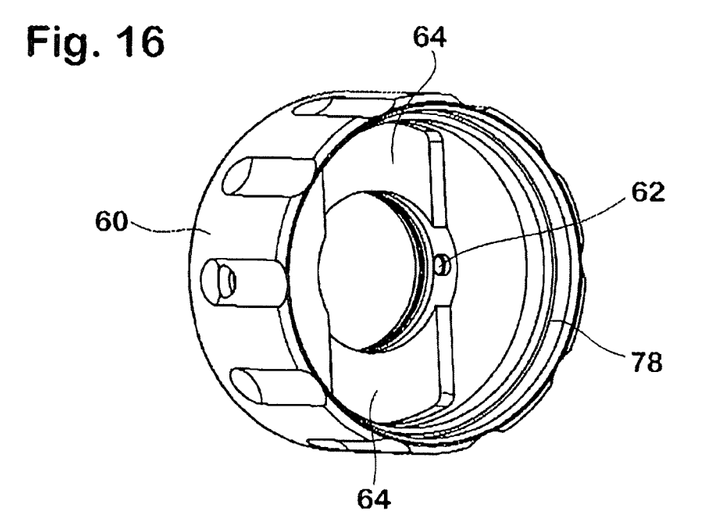
FIG. 16 shows an enlarged perspective view of the cap nut from FIG. 15.

When the proximal end of the inner sleeve part 34 on the side with the smallest diameter is pushed into the cap nut 60, then the pins 62 of the cap nut 60 touch the diagonal sides of the double-V-shaped contour 56. When the inner sleeve part 34 is pushed farther into the cap nut 60, the cap nut 60 is thereby rotated until the pins 62 are situated precisely in the indents of the double-V-shaped contour 56. The inner sleeve part 34 thereby assumes a firm position in the cap nut 60 both radially and axially.

Figure 17:
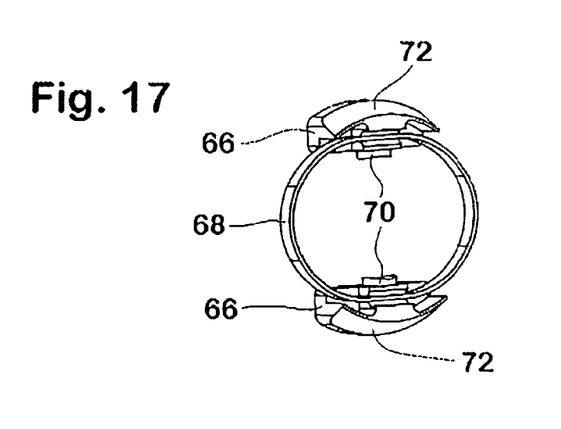
FIG. 17 shows an enlarged perspective view of the spring packet from FIG. 15.

Inside the cap nut 60 are situated two recesses 64, which extend perpendicular to the axis of the pins 62. One segment of one of two groove stones 66, which are fastened on opposite points on an oval spring 68, fits into each of the recesses 64 in order to form a spring packet as shown in FIG. 17. The oval spring 68 exerts a pretension force radially outward onto the groove stones 66 when the spring packet is seated in the cap nut 60, as shown in FIG. 18.

The groove stones 66 each bear a bolt extension 70, which fits precisely into a locking hole 56 of the inner sleeve part 34 and is flush with it when the pins 62 of the cap nut 60 are situated precisely in the indents of the double-V-shaped contour of the inner sleeve part 34. In addition, diagonally outward-pointing conical surfaces 72 are configured on the groove stones 66.

Figure 18:
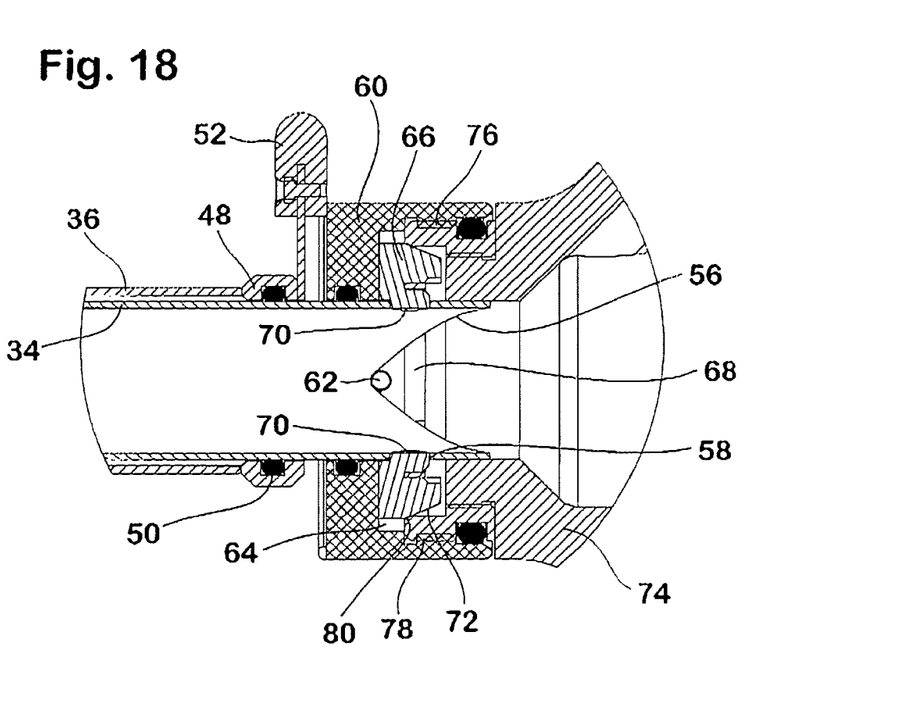
FIG. 18 shows a longitudinal sectional view of the trocar sleeve from FIG. 7 in the area of the fastening of the inner sleeve part on the head part.

The screw-in portion 74 of the head part 32 shown in FIGS. 15 and 18 bears an outer thread 76 that matches an inner thread 78 in the cap nut 60. When the screw-in portion 74 is rotated into the cap nut 60 while the inner sleeve part 34 and the spring packet are situated in it, then a conical portion 80 on the screw-in portion 74 presses against the conical surfaces 72 of the groove stones 66. The groove stones 66 are thereby moved inward against the spring force of the oval spring 68, so that the bolt extensions 70 engage in the locking holes 56 in the inner sleeve part 34 and thus lock the inner sleeve part 34 on the head part 32.

On releasing the threads 76 and 78 from one another, the groove stones 66 move outward so that the bolt extensions emerge from the locking holes 56 and the inner sleeve part 34, together with the outer sleeve part 36, can be withdrawn from the head part 32. Then the sleeve parts 34 and 36 can be separated from one another.

As can be recognized in FIG. 18, two O-rings insulate the cap nuts 60 from the inner sleeve part 34 or from the screw-in portion 74 of the head part 32.

Figure 19:
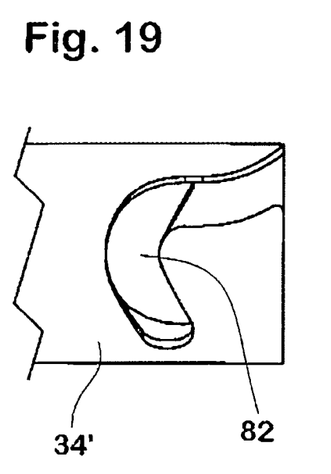
FIG. 19 shows a side view of a proximal resistance path in an inner sleeve part for a fastening on the head part by means of a type of bayonet lock.
Figure 20:
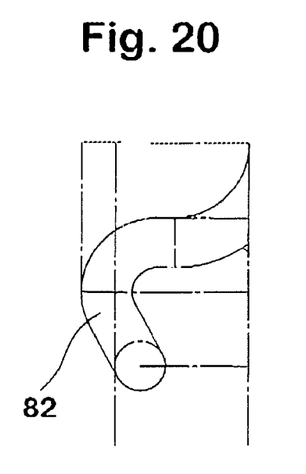
FIG. 20 shows an unfolding of the resistance path of the inner sleeve part from FIG. 19 into the plane.
Figure 21:
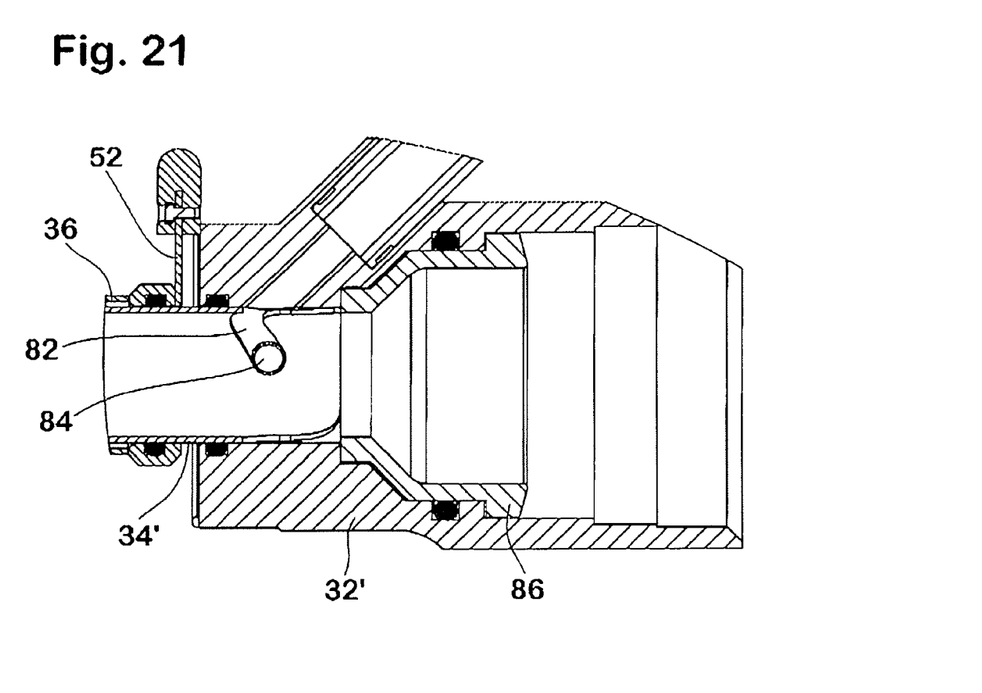
FIG. 21 shows a sectional view of the inner sleeve part from FIG. 19 and of a head part suited to it, which are connected with one another by a type of bayonet lock.

With reference to FIGS. 19 through 21, an example for a fastening of an inner sleeve part 34' on a head part 32' by means of a type of bayonet lock is now described, however with a distinction from a conventional bayonet lock in that the lock cannot be released by simple rotation of the connected parts in relation to one another.

The inner sleeve part 34' and the head part 32' are distinguished from the previously described inner sleeve part 34 and head part 32 only in the area of the fastening with one another. That is, in the area of the proximal end of the inner sleeve part 34' a resistance path 82 is hollowed out in its outer circumference, which seen from the side resembles FIG. 19 and appears unfolded into a plane as shown in FIG. 20. Protruding radially inward from the inner circumference of the head part 32' is a bayonet pin 84 (FIG. 21) that fits into the resistance path 82.

To fasten the inner sleeve part 34' on the head part 32', the head part 32' is pushed onto the inner sleeve part 34' in such a way that the bayonet pin 84 engages in the resistance path 82 and then is guided by it. If the head part 32' is then further pushed onto the inner sleeve part 34' and turned, then the head part 32' at first moves further in the distal direction by the inner sleeve part 34' until it is contiguous with the distally furthermost point of the resistance path 82. If the head part 32' is rotated further, then it moves again a short distance in the proximal direction. In this position the inner sleeve part 34' is fixed on the head part 32', in that a distancing sleeve 86 is inserted into the head part 32' starting from the proximal end of the head part 32' until it is contiguous with the inner sleeve part 34'. This is possible because the head parts 32 and 32' each comprise an unscrewable cap 30 (see FIG. 8) on the proximal end. By screwing the cap 30 back onto the head part 32' after inserting an insulation in the head part 32', the distancing sleeve 86 and thus the inner sleeve part 34' are fastened on the head part 32'. Because in this condition axial and radial movements overlap, no radial movement is possible between the inner sleeve part 34' and the head part 32' by the axial fastening.

In addition, in the area between maximum axial relative sliding and axial relative sliding in the assembled condition, as shown in FIG. 21, the metallic spring 52 of the actuation lever is elastically reshaped on the outer sleeve part 36. This provides a haptic feedback by the catch-locking of the bayonet lock.

Likewise as in the previously described embodiment, in the embodiment in FIGS. 7 through 21 as well, the trocar sleeve can be broken down easily and quickly into several components, facilitating their sterilization.

Characteristics of the embodiment in FIGS. 7 through 21 can also be combined with characteristics of the embodiment in FIGS. 1 through 6.

There follows a description of additional details and additional parts of the embodiment in FIGS. 7 through 21, which can also be applied in FIGS. 1 through 6.

Figure 22:
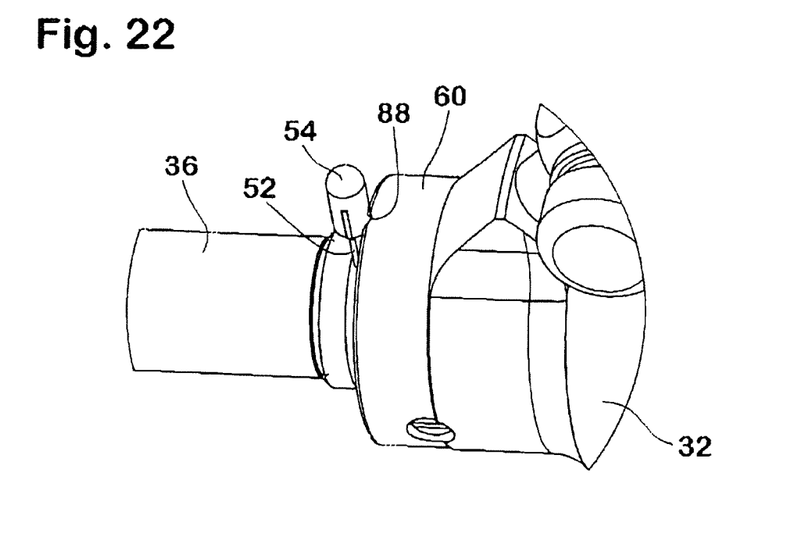
FIG. 22 shows a perspective view of the trocar sleeve portion shown in FIG. 18.

To indicate to the user the position in which the instrument is found, that is, the insertion position, in which the flange parts 44, 46 of the two sleeve parts 34, 36 point in the same direction, or the working position, in which the flange parts 44, 46 point in approximately contrary positions to one another, two partially cylindrical indentations, which are displaced from one another by 180 degrees, are foreseen on a distal plane surface of the head part 32 or 32' or of the cap nut 60. In FIG. 22, which gives a perspective view of the trocar sleeve portion shown in FIG. 18, these are two cylindrical indentations 88 for the insertion position or the working position, only one of which is visible in the drawing, on the cap nut 60. As long as the synthetic cap 54 of the actuation lever is situated in one of these indentations 88, its metallic spring 52 is not impacted. If the outer sleeve part 36 is rotated by means of the actuation lever, the actuation lever must overcome the rim of the corresponding indentation 88. Thus the axial distance between the head part 32 and the outer sleeve part 36 changes, and the metallic spring 52 is pretensed. As soon as the actuation lever moves over one of the indentations 88, it catches easily therein, as the metallic spring 52 is relaxed.

Figure 8:
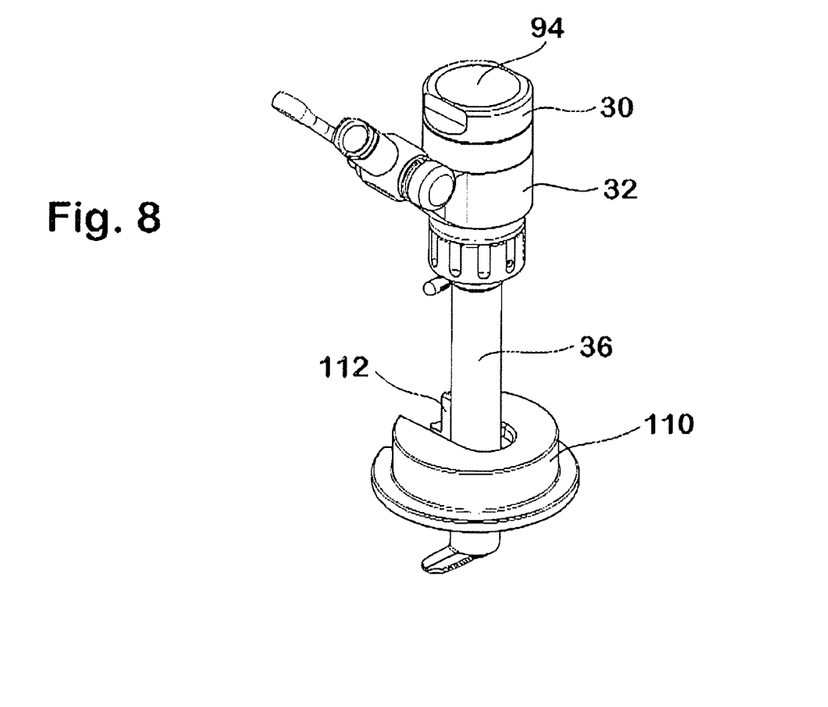
FIG. 8 shows another perspective view of the trocar sleeve from FIG. 7, on which a securing element is additionally installed.
Figure 23:
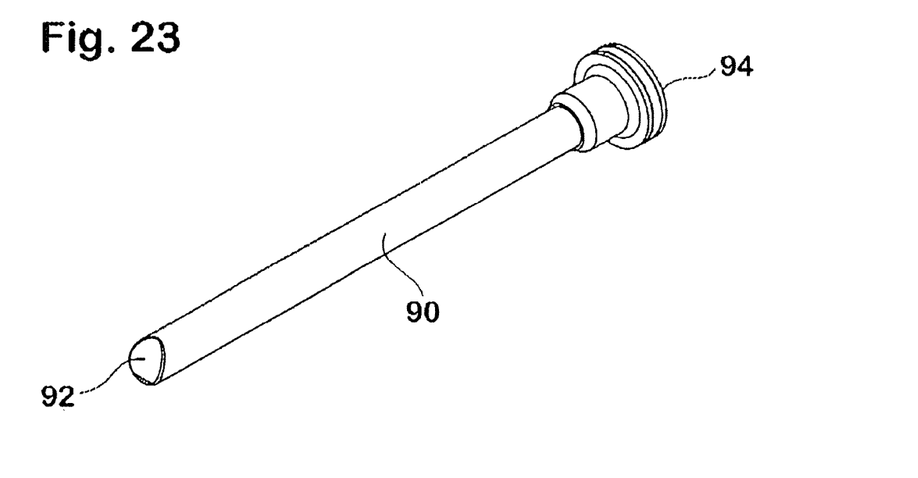
FIG. 23 shows a perspective view of a trocar mandrel for insertion into the shown trocar sleeve.

FIG. 23 shows a trocar mandrel 90, which is especially suited for inserting the described trocar sleeves in a body. The trocar mandrel 90 has, instead of the otherwise customary sharp point, a blunt distal end 92 with a slightly curved front surface with small fibers or roundings in the transition to the cylindrical shaft of the trocar mandrel 90. The contour of the distal end 92 of the trocar mandrel 90 ends essentially flush with the contour of the distal end of the trocar sleeve, which can be recognized more precisely in FIG. 14, when the trocar mandrel 90 is completely inserted in the trocar sleeve, as can be seen in FIG. 7. This condition can be recognized by an operator from the fact that the proximal end 94 of the trocar mandrel 90 ends flush with the proximal end of the trocar head 32, as can be seen in FIG. 8.

To be used, the trocar mandrel 90 is inserted from the proximal end through the trocar sleeve in order thereby to close its distal end. The spatula formed by the flange parts 44 and 46 (or 14 and 16) is inserted in a scalpel cut, while the trocar is held diagonally above the epithelium. The trocar is pivoted into perpendicular position, and the sleeve parts 34 and 36 and thus the flange parts 44 and 46 are rotated with respect to one another by means of the actuation lever, so that the trocar is inserted atraumatically in the body opening. Then the trocar mandrel 90 can be withdrawn from the trocar sleeve. The trocar sleeve is now open in order to perform a minimally invasive procedure through the trocar sleeve.

Then the flange parts 44 and 46 are secured on the outside of the epithelium with a securing element that surrounds the outer sleeve part 36 and can be slid axially along the outer sleeve part 36 by overcoming or switching off its clamping force. Even better suited for this purpose than the previously described one-piece rubber disc with gap are securing elements, as are described below.

Figure 24:
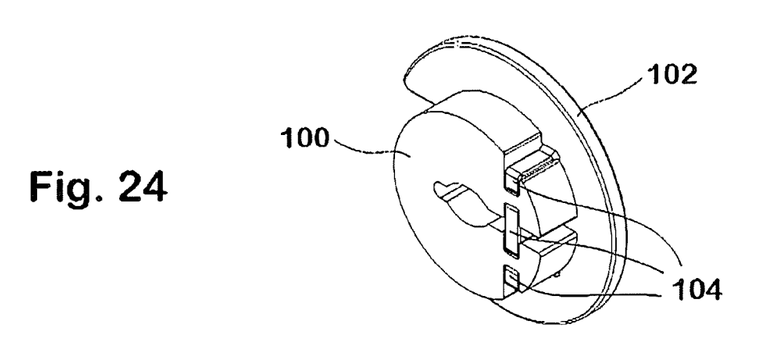
FIG. 24 shows a securing element consisting only partly of an elastic material, in a perspective view.

The securing element shown in FIG. 24 can be broken down into two parts, namely a disc-shaped part 100, with gap, of an elastic material such as silicon that has a somewhat smaller inner diameter than the outer diameter of the outer sleeve part 36, and a support plate 102, with gap, of a rigid material such as steel. Protruding at a right angle from the support plate 102 are extensions 104 that fit in matching recesses in the elastic part 100. Said extensions 104 hold the elastic part 100 firmly to the rigid support plate 102 and stabilize it in order achieve sufficient clamping force. The elastic part 100 and the support plate 102 have sufficiently extensive gaps so that they can be separately pushed laterally onto the outer sleeve part 36 and then connected together in the axial direction.

Figure 25:
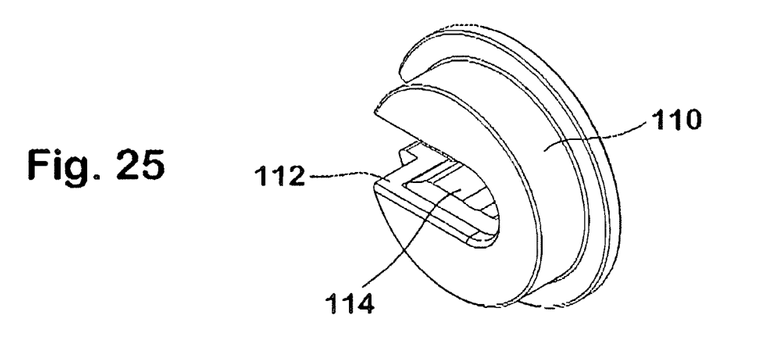
FIG. 25 shows another securing element consisting only partly of an elastic material, in a perspective view.

The securing element shown in FIG. 25 can also be broken down into two parts, namely a ring-shaped enclosure 110 of a rigid material such as steel with a U-shaped gap 112, and an insert 114 of an elastic material such as silicon that is inside the gap 112 and can be fixed somewhat in the gap 112 by form-locking or force-locking but is removable. The enclosure 110 stabilizes the insert 114 in order to produce sufficient clamping force. The enclosure 110 and insert 114 can be pushed simultaneously or sequentially onto the outer sleeve part 36 and then axially slid along on it into the desired position as illustrated in FIG. 8.

Figure 26:
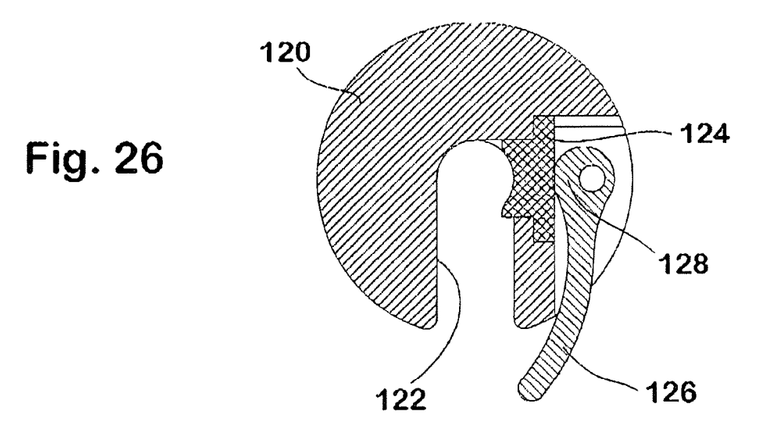
FIG. 26 shows a securing element consisting only of rigid parts, in a sectional view.

The securing element shown in FIG. 26 cannot be dismantled and consists of an approximately rigid plate 120 with a radial gap 122, a clamping element 124 that can be slid in the direction toward the inner end of the gap 122, and an actuation lever 126, which is mounted to pivot on the plate 120 and comprises at its base a cam 128 that grips on the clamping element 124. After this securing element has been pushed laterally onto the outer sleeve part 36, the clamping element 124 is pressed against the outer sleeve part 36 by pivoting the actuation lever 126 and remains in this position by gripping action of the cam 128 on the clamping element 124.

What is claimed is:

1. A trocar assembly for minimally invasive surgery, comprising
   a first sleeve part, which has essentially the shape of a straight tubular piece with a longitudinal axis, having a head part on a proximal end, and
   a second sleeve part, which at least partly surrounds the first sleeve part and is rotatable around the first sleeve part,
   wherein the first sleeve part and the second sleeve part each comprise on their distal axial ends a flange part that extends radially outward at an angle of less than 180 degrees from the respective sleeve part, and
   wherein the second sleeve part is adapted to rotate its flange part along a plane approximately perpendicular to the longitudinal axis between two end positions, which are approximately 180 degrees apart with respect to the longitudinal axis, such that a first end position corresponds to an insertion position in which the flange parts of the first and second sleeve parts point approximately in the same direction, and such that a second end position corresponds to a working position in which the flange parts of the first and second sleeve parts point approximately in opposite directions to secure the trocar assembly in a body opening, the flange parts situated approximately in the plane perpendicular to the longitudinal axis in both the insertion position and working position.

2. The trocar assembly according to claim 1, wherein in the insertion position the two flange parts are situated one above the other.

3. The trocar assembly according to claim 1, wherein the head part comprises an insulation for gas-tight insertion of an instrument into the trocar assembly and a fluid connecting support, guide and locking elements in which a proximal end of the second sleeve part is guided for rotation around the first sleeve part and can be locked at least in an end position of the second sleeve part, which corresponds to the working position.

4. The trocar assembly according to claim 1, wherein the section of the second sleeve part that surrounds the first sleeve part has essentially the shape of a straight tubular piece.

5. The trocar assembly according to claim 1, wherein the section of the second sleeve part that surrounds the first sleeve part has essentially the shape of a half of a tube that is divided in half lengthwise.

6. The trocar assembly according to claim 5, wherein the cross-section of the second sleeve part perpendicular to the longitudinal axis is a circular arc, which is larger than a semicircle.

7. The trocar assembly according to claim 1, wherein each of the two sleeve parts has essentially the shape of a full tube.

8. The trocar assembly according to claim 7, wherein the first sleeve part is detachably fastened on the head part and the two sleeve parts are configured in such a way that the second sleeve part can be assembled on the first sleeve part and disassembled from it when the first sleeve part is detached from the head part.

9. The trocar assembly according to claim 8, wherein the flange parts of the first and second sleeve parts together have a U-shaped radial contour in the insertion position, as seen in a plane perpendicular to the longitudinal axis.

10. The trocar assembly according to claim 8, wherein the detachable fastening of the first sleeve part on the head part includes a screw-in lock.

11. The trocar assembly according to claim 8, wherein the detachable fastening of the first sleeve part on the head part includes a type of bayonet lock.

12. The trocar assembly according to claim 1 further comprising a trocar mandrel that fits in the first sleeve part, wherein the trocar mandrel has a blunt distal end whose contour ends essentially flush with the contour of the distal end of the first sleeve part when the trocar mandrel is inserted completely into the first sleeve part.

13. The trocar assembly according to claim 1 further comprising a securing element that is placed so as to surround the first and second sleeve parts and to secure the flange parts in the direction of the longitudinal axis.

14. The trocar assembly according to claim 13, wherein the securing element is a one-piece rubber disc with a gap.

15. The trocar assembly according to claim 13, wherein the securing element comprises a rigid element with a gap sized to match the outer diameter of the outer sleeve part and an elastic element that is detachable from the rigid element.

16. The trocar assembly according to claim 13, wherein the securing element comprises a plate with a gap sized to fit the outer diameter of the outer sleeve part, a clamping element that can be slid on the plate for the outer sleeve part and an actuation element mounted on the plate for the slidable clamping element.

17. The trocar assembly according to claim 1 wherein a medical instrument is inserted through the tubular piece of the first sleeve part to perform a surgical procedure.

18. A trocar assembly for minimally invasive surgery, comprising
   a first sleeve part, which has essentially the shape of a straight tubular piece with a longitudinal axis, having a head part on a proximal end, and
   a second sleeve part, which at least partly surrounds the first sleeve part and is rotatable around the first sleeve part,
   wherein the first sleeve part and the second sleeve part each comprise on their distal axial ends a flange part that extends radially outward at an angle of less than 180 degrees from the respective sleeve part to secure the trocar assembly in a body opening when in a working position, and
   wherein the flange parts are connected as a single piece with the respective sleeve part and/or are each approximately 1 mm thick.

19. The trocar assembly according to claim 18, wherein the second sleeve part is adapted to rotate its flange part along a plane approximately perpendicular to the longitudinal axis between two end positions, which are approximately 180 degrees apart with respect to the longitudinal axis, such that a first end position corresponds to an insertion position in which the flange parts of the first and second sleeve parts point approximately in the same direction, and such that a second end position corresponds to the working position in which the flange parts of the first and second sleeve parts point approximately in opposite directions.

20. A trocar assembly for minimally invasive surgery, comprising
   a first sleeve part, which has essentially the shape of a straight tubular piece with a longitudinal axis, having a head part on a proximal end, and
   a second sleeve part, which at least partly surrounds the first sleeve part and is rotatable around the first sleeve part,
   wherein the first sleeve part and the second sleeve part each comprise on their distal axial ends a flange part that extends radially outward at an angle of less than 180 degrees from the respective sleeve part to secure the trocar assembly in a body opening when in a working position, and
   wherein the flange parts have approximately U-shaped radial contours, as seen in a plane perpendicular to the longitudinal axis, such that the distance between the U-shape radial contours of the flange parts is approximately equal to the diameter of the first or of the second sleeve part.

21. The trocar assembly according to claim 20, wherein the second sleeve part is adapted to rotate its flange part along a plane approximately perpendicular to the longitudinal axis between two end positions, which are approximately 180 degrees apart with respect to the longitudinal axis, such that a first end position corresponds to an insertion position in which the flange parts of the first and second sleeve parts point approximately in the same direction, and such that a second end position corresponds to the working position in which the flange parts of the first and second sleeve parts point approximately in opposite directions.

* * * * *